(12) United States Patent
May et al.

(10) Patent No.: US 7,045,628 B2
(45) Date of Patent: May 16, 2006

(54) SYNTHESIS OF 2-ARYL-1-NAPHTHOL DERIVATIVES VIA A TANDEM PALLADIUM CATALYZED ARYLATION AND DEHYDROGENATION

(75) Inventors: Scott Allan May, Noblesville, IN (US); Thomas Michael Wilson, Speedway, IN (US); Tony Yantao Zhang, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 526 days.

(21) Appl. No.: 10/432,091

(22) PCT Filed: Nov. 15, 2001

(86) PCT No.: PCT/US01/42945

§ 371 (c)(1),
(2), (4) Date: May 20, 2003

(87) PCT Pub. No.: WO02/44119

PCT Pub. Date: Jun. 6, 2002

(65) Prior Publication Data

US 2004/0133047 A1    Jul. 8, 2004

(51) Int. Cl.
*C07D 295/03* (2006.01)
(52) U.S. Cl. .................. 546/194; 548/568; 564/123
(58) Field of Classification Search ................ 546/194; 548/568; 564/123
See application file for complete search history.

(56) References Cited

U.S. PATENT DOCUMENTS

| 5,916,916 A | 6/1999 | Hauser et al. |
| 5,929,090 A | 7/1999 | Hauser et al. |
| 5,998,401 A | 12/1999 | Palkowitz |
| 6,593,345 B1 | 7/2003 | Bryant et al. |

FOREIGN PATENT DOCUMENTS

EP        0826679 B1     11/2001

*Primary Examiner*—Kamal A. Saeed
*Assistant Examiner*—Michael Barker
(74) *Attorney, Agent, or Firm*—Gary M. Birch; Gilbert T. Voy

(57) ABSTRACT

The present invention relates to a one-pot process for preparing a compound of formula I: I; by reacting a compound of formula II with a compound of formula III: in the presence of a suitable solvent, a suitable base, a palladium catalyst and a suitable ligand.

10 Claims, No Drawings

SYNTHESIS OF 2-ARYL-1-NAPHTHOL DERIVATIVES VIA A TANDEM PALLADIUM CATALYZED ARYLATION AND DEHYDROGENATION

This application is 35 USC 371 of PCT/US01/42945, filed Nov. 15, 2001 which claims the benefit of U.S. Provisional application No. 60/253,502 filed Nov. 28, 2000.

BACKGROUND OF THE INVENTION

Naphthol compounds of the general formula:

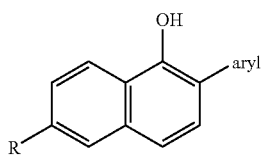

are versatile intermediates to pharmaceutically active compounds (see, e.g., U.S. Pat. Nos. 5,916,916, 5,929,090 and 5,998,401).

According to the procedures described in the above mentioned patents, the naphthol intermediates are constructed via a four step sequence beginning from an arylacetic acid. Said construct employs undesirable reagents in chemical processing such as aluminum chloride ($AlCl_3$) and 2,3-dichloro-5,6-dicyanobenzoquinone (DDQ) under strong basic and acidic conditions.

BRIEF SUMMARY OF THE INVENTION

The present invention relates to a process for preparing a compound of formula I:

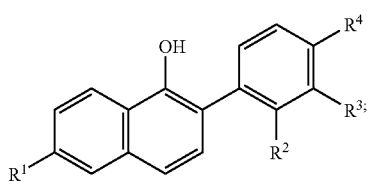

wherein:

$R^1$, $R^2$, $R^3$ and $R^4$ are independently H, OH or OPg where Pg is a hydroxy protecting group;

which includes reacting a compound of formula II:

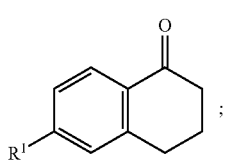

with a molar excess, relative to the compound of formula II, of a compound of formula III:

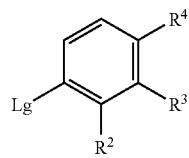

wherein Lg is a leaving group;

in the presence of a suitable solvent, a suitable base, a palladium catalyst and a suitable ligand; at a temperature between 35° C. and the reflux temperature of the reaction mixture.

DETAILED DESCRIPTION OF THE INVENTION

General terms used in the description of chemical formulas bear their usual meanings. For example, the term "$C_1$–$C_6$ alkyl" refers to a straight, branched or cyclic (in the case of $C_3$–$C_6$ alkyl) aliphatic alkyl chain of 1 to 6 carbon atoms including, methyl, ethyl, propyl, isopropyl, cyclopropyl, n-butyl, s-butyl, t-butyl, cyclobutyl, pentyl, cyclopentyl, n-hexyl, cyclohexyl and the like.

The term "hydroxy protecting group" is well known to those skilled in the art. Representative hydroxy protecting groups can be found in Greene, et al., *Protective Groups in Organic Synthesis*, John Wiley & Sons, Inc., New York, N.Y. 1991. Such groups include benzyl, CO-phenyl, $CO_2$-phenyl, trialkylsilyl such as t-butyldimethylsilyl, $C_1$–$C_6$ alkyl, CO($C_1$–$C_6$ alkyl), $CO_2$($C_1$–$C_6$ alkyl), and $SO_2$($C_1$–$C_6$ alkyl) where said phenyl moiety is optionally substituted with $C_1$–$C_4$ alkyl.

The term "leaving group" refers to an atom, or group of atoms that in the aggregate are capable of being activated to oxidative insertion by the palladium catalyst, i.e., to the palladium (0) species. Examples of such leaving groups include halides such as Cl, Br and I; sulfonates (a group of the general formula $OSO_2R^5$ where $R^5$ is optionally substituted $C_1$–$C_6$ alkyl or optionally substituted phenyl) such as methanesulfonate, trifluoromethanesulfonate or toluenesulfonate; and phosphonates (a group of the general formula $OPO(OR^5)2$ where $R^5$ is $C_1$–$C_6$ alkyl or phenyl.

The term "suitable solvent" refers to any solvent, or mixture of solvents, inert to the ongoing reaction that sufficiently solubilizes the reactants to afford a medium within which to effect the desired reaction. Suitable solvents include methylene chloride, chloroform, 1,2-dichloroethane, diethyl ether, acetonitrile, ethyl acetate, 1,3-dimethyl-2-imidazolidinone, 1,4-dioxane, tetrahydrofuran, dimethylformamide, toluene, chlorobenzene, dimethylsulfoxide, N-methylpyrrolidinone, dimethylacetamide, hexamethylphosphoramide, toluene, xylene, halophenyl solvents such as chlorobenzene, etheral solvents such as glyme, diglyme and ethyleneglycol diether ether, mixtures thereof, and the like.

The term "suitable base" refers to a base that is capable of effecting a deprotonation of the hydrogen alpha to the ketone in the compound of formula II, i.e., a base that can provide an in situ enolate of the formula:

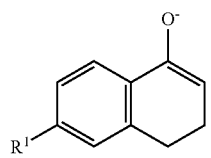

Examples of bases that can accomplish this enolization include alkyl metals (for example, n-butyl lithium, s-butyl lithium, and t-butyl lithium or ethyl magnesium bromide and the like), metal amides such as lithium diisopropyl amide, potassium, lithium, or sodium salts of dimethylsulfoxide or hexamethydisilazane, metal hydrides (for example, sodium, lithium, or potassium hydride), metal alkoxides (for example, sodium, lithium or potassium t-butoxide) or cesium carbonate.

The term "palladium catalyst" refers to a source of Pd(0). Suitable palladium catalysts for use in the process of the present invention include elemental palladium, salts and complexes of palladium, and palladium on solid supports such as palladium on carbon or palladium on aluminum oxide.

The term "suitable ligand" refers to a suitable compound containing P, S, N, and C than can donate a pair of electrons to the palladium catalyst. Suitable ligands include alkyl or aryl phosphines such as 2,2'-bis(diphenylphosphino)-1,1'-binaphthyl (BINAP), triphenylphosphine and the like.

The process of the present invention consists of a two stage sequence. The first step of the process involves a palladium catalyzed alpha-arylation of tetralone II with a molar excess of the compound of formula III. The arylated product is then oxidized with the excess formula III compound serving as stoichiometric oxidant. This oxidation can occur simultaneously or may be effected by raising the temperature of the reaction mixture or by adding triphenyl phosphine to the reaction mixture. This novel process is illustrated in Scheme 1 below.

Scheme 1

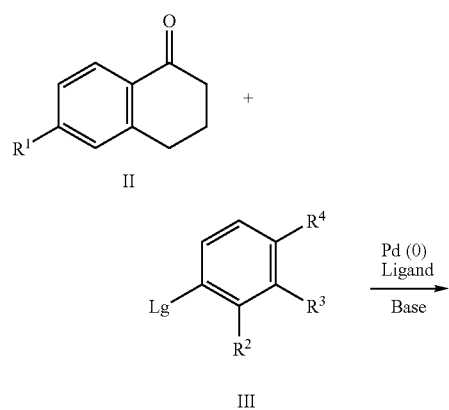

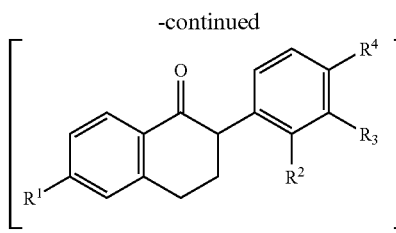

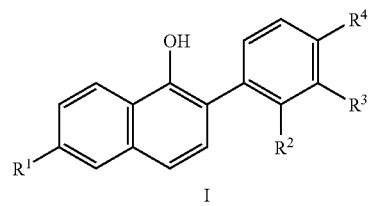

A compound of formula II may be added to a solution or suspension of a suitable base, such as sodium tert-butoxide, in a suitable solvent, such as 1,4-dioxane in the presence of the formula III compound. A palladium catalyst, such as palladium acetate, and a suitable ligand, such as BINAP, may then be added to the reaction followed by stirring/agitation of the resulting mixture for a time and at a temperature sufficient to complete the coupling and oxidation reactions. The resulting compound of formula I may be isolated by standard techniques.

In general, the reactants may be combined at ambient temperature. Once the reactants are combined, the reactions (coupling and oxidation) are typically performed at elevated temperatures with the coupling reaction generally requiring less heat. The coupling reaction is typically performed between 35° C. and the reflux temperature of the reaction mixture. More typically, the coupling reaction is performed between 50° C. and 120° C. with a reaction temperature range of 60° C. to 100° C. being more typical. Once the coupling has been effected, the oxidation reaction generally requires additional heat to effect the transformation. Therefore, the oxidation reaction is typically performed between 50° C. and the reflux temperature of the reaction mixture. More typically, the oxidation reaction is performed between 80° C. and 160° C. with a reaction temperature range of 90° C. to 110° C. being more typical.

As an alternative to applying additional heat to the system, a phosphine, such as triphenylphosphine may be added to the coupled product mixture to promote the oxidation at temperatures more similar to those required for the coupling reaction.

Typically, a molar excess of base (from 2 to about 6 equivalents, relative to the compound of formula II, is used. More typically, 3.0 to about 6.0 equivalents are employed while most typically, 3.5 to about 4.5 equivalents are employed. A molar excess of between 3.8 and 4.2 is most preferred. A molar excess of the compound of formula III (1.01 to about 4.0 equivalents), relative to the compound of formula II, is typically used. More typically, 1.01 to about 3.25 equivalents are employed while most typically, 1.75 to about 2.5 equivalents are employed. The palladium catalyst is employed catalytically (0.005–10 mole percent) relative to the compound of formula II. More typically, 0.05 to about 5 mole percent is employed while most typically, 0.5 to about 1.5 mole percent is employed. The amount of ligand used in the present process is dependent upon the amount of palladium catalyst used. A monodentate ligand requires approximately 2 equivalents of ligand relative to the palladium catalyst whereas a bidentate ligand would require only 1 equivalent.

The time required to effect the overall transformation will be dependent upon the temperature at which the reactions are run. Therefore, the progress of the reactions should be monitored via conventional techniques, e.g., HPLC, to determine when the reactions are substantially complete. Monitoring the progress of chemical reactions is well within the ordinarily skilled artisan's capability.

Preferred compounds of formula II for use in the present process are those where $R^1$ is hydroxy, methoxy, isopropoxy or benzyloxy, particularly benzyloxy. Preferred compounds of formula III for use in the present process are those where $R^2$ is hydrogen and $R^3$ and $R^4$ are independently selected from H, benzyloxy, methoxy or isopropoxy. Thus, preferred products of the above reaction include, but are not limited to, 1-hydroxy-2-(4-methoxyphenyl)-6-(methoxy)naphthalene, 1-hydroxy-2-(4-methoxyphenyl)-6-(isopropoxy)naphthalene, 1-hydroxy-2-(4-methoxyphenyl)-6-(benzyloxy)naphthalene, 1-hydroxy-2-(4-methoxyphenyl)-6-(hydroxy)naphthalene, 1-hydroxy-2-(4-ispropoxyphenyl)-6-(hydroxy)naphthalene, 1-hydroxy-2-(4-benzyloxyphenyl)-6-(hydroxy)naphthalene, 1-hydroxy-2-(4-isopropoxyphenyl)-6-(methoxy)naphthalene, 1-hydroxy-2-(4-isopropoxyphenyl)-6-(isopropoxy)naphthalene, 1-hydroxy-2-(4-isopropoxyphenyl)-6-(benzyloxy)naphthalene, 1-hydroxy-2-(4-benzyloxyphenyl)-6-(methoxy)naphthalene, 1-hydroxy-2-(4-benzyloxyphenyl)-6-(isopropoxy)naphthalene, and 1-hydroxy-2-(4-benzyloxyphenyl)-6-(benzyloxy)naphthalene.

In a preferred embodiment, a compound of formula I may be used to prepare pharmaceutically useful compounds such as that described in U.S. Pat. No. 5,998,401, that is, a compound of formula IV:

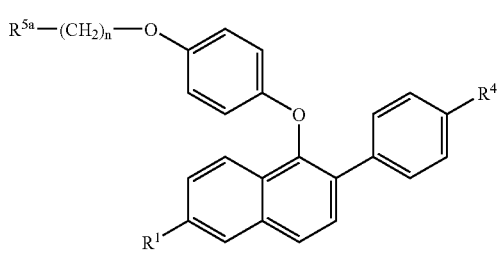

wherein $R^1$ and $R^4$ are as described above;

$R^{5a}$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino; and n is 2 or 3; and or a pharmaceutically acceptable salt thereof;

European Patent Application No. EP 0 826 679, that is, a compound of formula V:

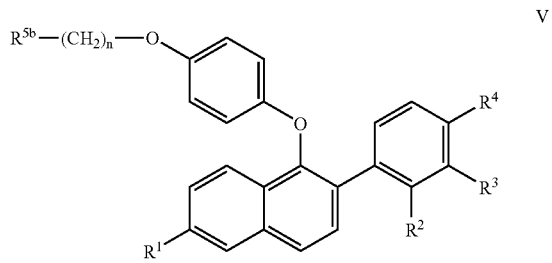

wherein n, $R^1$, $R^2$, $R^3$ and $R^4$ are as described above with the proviso that both $R^3$ and $R^4$ cannot be hydrogen; and $R^{5b}$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt or solvate thereof; and U.S. Pat. No. 5,929,090, that is, a compound of formula VI

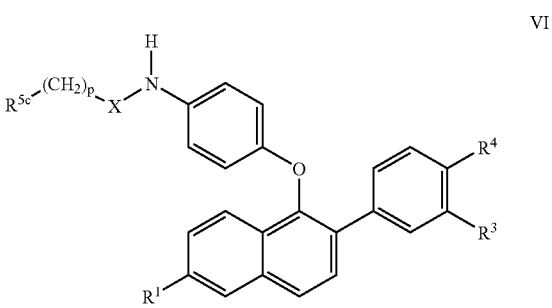

or a pharmaceutically acceptable salt thereof wherein p is 1, 2, or 3;

$R^1$, $R^3$ and $R^4$ are as described above;

$R^{5c}$ is selected from the group consisting of 1-piperidinyl, 1-pyrrolidinyl, methyl-1-pyrrolidinyl, dimethyl-1-pyrrolidino, 4-morpholino, dimethylamino, diethylamino, diisopropylamino, and 1-hexamethyleneimino; and X is absent or is selected from the group consisting of —C(O)— and —SO$_2$—;

the teachings of which are herein incorporated by reference. Methods for converting a compound of formula I to these and other pharmaceutically useful compounds may be found in said U.S. patents and patent applications.

In a particularly preferred embodiment, a compound of formula I may be used to prepare a compound of formula VII, VIII, and IX:

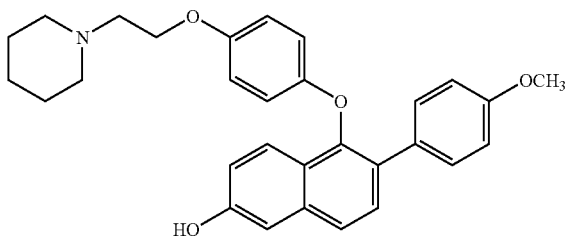

VII

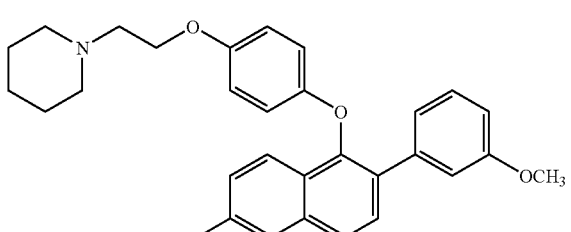

VIII

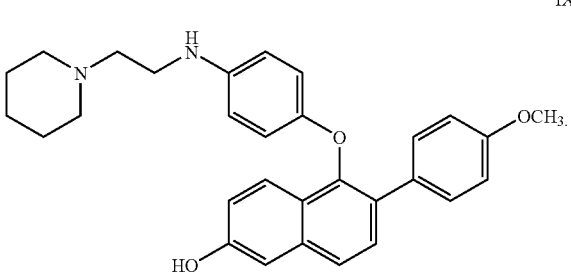

IX

Compounds of formula II are known in the art and are generally commercially available or are prepared by methods well known in the art from readily available starting materials.

EXAMPLES

Example 1

1-Hydroxy-2-(4-methoxyphenyl)-6-(benzyloxy) naphthalene

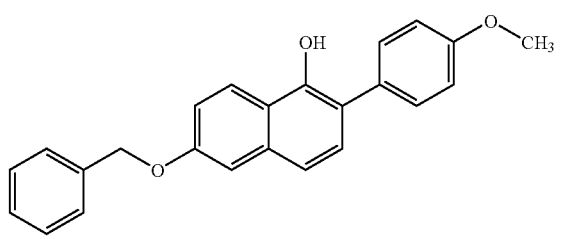

Twelve liters of 1,4-dioxane were vacuum degassed and then combined with sodium tert-butoxide (1523 g, 15.84 mol), 4-bromoanisole (1845 g, 9.86 mol) and 3,4-dihydro-6-(phenylmethoxy)-1(2H)-naphthalenone (1002 g, 3.97 mol). The resulting red slurry was again degassed by pulling vacuum and purging the system with nitrogen. Palladium acetate (8.90 g, 0.0396 mol) and 2,2'-bis(diphenylphosphino)-1,1'-binaphthyl (25.9 g, 0.0416 mol) were added and the mixture was heated to 70° C. After 2.5 hours the temperature was increased to 100° C. and this temperature was maintained for an additional 5 hours. The mixture was allowed to cool to ambient temperature before quenching with 6 liters of 3 M HCl. The layers were allowed to separate and the aqueous phase was extracted with 2 liters of ethyl acetate. The organic phases were combined and dried with 500 g of sodium sulfate then concentrated to a red solid. The solid was combined with 4 liters of toluene and stirred at 60° C. for 1 hour then cooled to ambient temperature. The solids were collected by filtration, washed with toluene and dried in vacuo to provide 564 g (40%) of the title compound. $H^1$ NMR (CDCl$_3$, 500 MHz) 8.20 (d, J=9.1 Hz, 1H), 7.50 (d, J=7.3 Hz, 2H), 7.44 (d, J=8.7 Hz, 2H), 7.42 (t, J=7.3 Hz, 2H), 7.35 (m, 2H), 7.29 (d, J=8.5 Hz, 1H), 7.25 (dd, J=2.5, 9.1 Hz, 1H), 7.20 (d, J=2.5, 1H), 7.07 (d, J=8.7 Hz, 2H), 5.75 (s, 1H), 5.20 (s, 2H), 3.88 (s, 3H).

What is claimed is:

1. A process for preparing a compound of formula I:

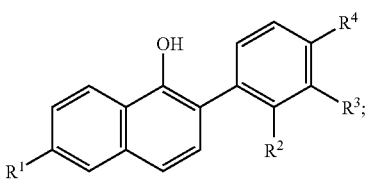

wherein:

R1, R2, R3 and R4 are independently H, OH or OPg where Pg is a hydroxy protecting group;

which includes reacting a compound of formula II:

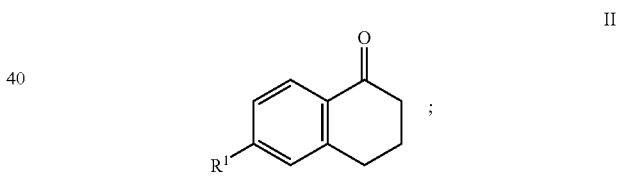

with a molar excess, relative to the compound of formula II, of a compound of formula III:

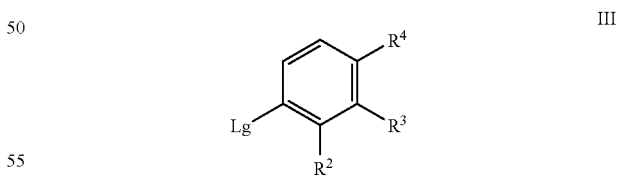

wherein Lg is a leaving group;

in the presence of a suitable solvent, a suitable base, a palladium catalyst and a suitable ligand; at a temperature between 35° C. and the reflux temperature of the reaction mixture.

2. The process of claim 1 wherein the compound of formula II is a compound where $R^2$ is benzyloxy, methoxy or isopropoxy and the compound of formula III is a compound where $R^2$ is hydrogen; and $R^3$ and $R^4$ are independently H, benzyloxy, methoxy or isopropoxy.

3. The process of claim 2 wherein the compound of formula II is a compound where $R^1$ is benzyloxy and wherein the compound of formula m is a compound where $R^3$ is hydrogen and $R^4$ is methoxy.

4. The process of claim 3 wherein the solvent is 1,4-dioxane, the base is sodium tert-butoxide, the palladium catalyst is palladium acetate, the ligand is 2,2'-bis(diphenylphosphino)-1,1'-binaphthyl and the temperature is the reflux temperature of the reaction mixture.

5. In a process for preparing a compound of formula IV:

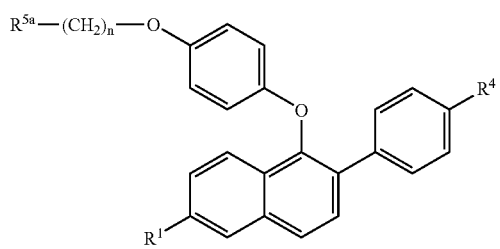

IV wherein
  $R^1$ and $R^4$ are independently H, OH or OPg where Pg is a hydroxy protecting group;
  $R^{5a}$ is 1-piperidinyl, 1-pyrrolidinyl, methyl-1-pyrrolidinyl, dimethyl-1-pyrrolidino, 4-morpholino, dimethylamino, diethylamino, diisopropylamino, or 1-hexamethyleneimino; and n is 2 or 3; and or a pharmaceutically acceptable salt thereof;
which comprises the process of claim 1.

6. The process of claim 5 wherein the compound of formula IV is of the formula VII:

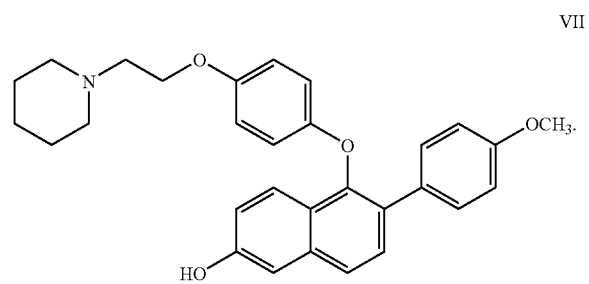

VII

7. In a process for preparing a compound of formula V:

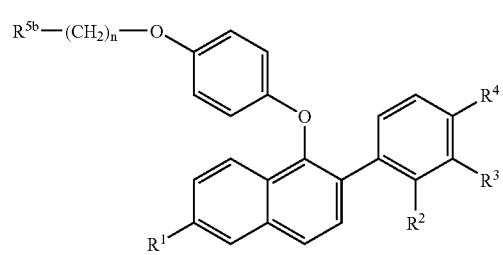

V wherein
  $R^1$, $R^2$, $R^3$ and $R^4$ are independently H, OH or OPg where Pg is a hydroxy protecting group with the proviso that both $R^3$ and $R^4$ cannot be hydrogen;

n is 2 or 3; and
  $R^{5b}$ is 1-piperidinyl, 1-pyrrolidinyl, methyl-1-pyrrolidinyl, dimethyl-1-pyrrolidinyl, 4-morpholino, dimethylamino, diethylamino, or 1-hexamethyleneimino; or a pharmaceutically acceptable salt or solvate thereof;
which comprises the process of claim 1.

8. The process of claim 7 wherein the compound of formula V is of the formula VIII:

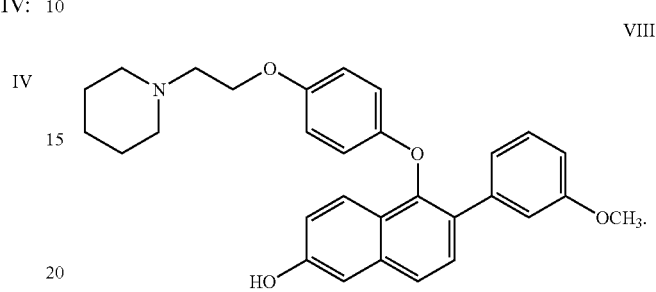

VIII

9. In a process for preparing a compound of formula VI:

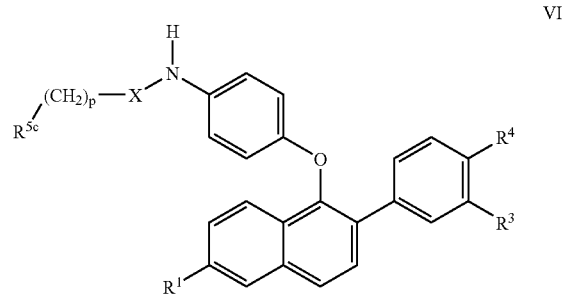

VI or a pharmaceutically acceptable salt thereof wherein
  p is 1,2, or 3;
  $R^1$, $R^3$ and $R^4$ are independently H, OH or OPg where Pg is a hydroxy protecting group;
  $R^{5c}$ is selected from the group consisting of 1-piperidinyl, 1-pyrrolidinyl, methyl-1-pyrrolidinyl, dimethyl-1-pyrrolidino, 4-morpholino, dimethylamino, diethylamino, diisopropylamino, and 1-hexamethyleneimino; and
  X is absent or is selected from the group consisting of —C(O)— and —SO$_2$—; which comprises the process of claim 1.

10. The process of claim 9 wherein the compound of formula VI is of the formula IX:

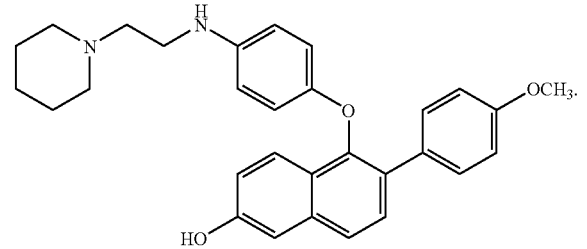

IX

* * * * *